US009826169B2

(12) United States Patent
Suzuki et al.

(10) Patent No.: US 9,826,169 B2
(45) Date of Patent: Nov. 21, 2017

(54) IMAGE PICKUP APPARATUS, IMAGE PROCESSING APPARATUS, AND METHOD FOR ACTIVATING IMAGE PICKUP APPARATUS

(71) Applicant: OLYMPUS CORPORATION, Tokyo (JP)

(72) Inventors: Tatsuhiko Suzuki, Hino (JP); Tomoki Iwasaki, Fuchu (JP); Susumu Hashimoto, Hachioji (JP); Toshihiro Hamada, Fuchu (JP); Yuji Kutsuma, Kokubunji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/335,652

(22) Filed: Oct. 27, 2016

(65) Prior Publication Data

US 2017/0078586 A1 Mar. 16, 2017

Related U.S. Application Data

(63) Continuation of application No. PCT/JP2015/082132, filed on Nov. 16, 2015.

(30) Foreign Application Priority Data

Nov. 21, 2014 (JP) .................................. 2014-236899

(51) Int. Cl.
*H04N 7/18* (2006.01)
*H04N 5/232* (2006.01)
(Continued)

(52) U.S. Cl.
CPC ........... *H04N 5/23296* (2013.01); *A61B 1/00* (2013.01); *A61B 1/04* (2013.01); *G02B 23/24* (2013.01);
(Continued)

(58) Field of Classification Search
None
See application file for complete search history.

(56) References Cited

U.S. PATENT DOCUMENTS

2011/0275889 A1  11/2011  Kase et al.
2013/0050454 A1*  2/2013  Ogasawara ........ A61B 1/00009
                                                      348/65

(Continued)

FOREIGN PATENT DOCUMENTS

EP        2497406 A1    9/2012
EP        2929830 A1   10/2015
(Continued)

OTHER PUBLICATIONS

International Search Report dated Feb. 2, 2016 issued in PCT/JP2015/082132.

*Primary Examiner* — James M Anderson, II
(74) *Attorney, Agent, or Firm* — Scully, Scott, Murphy & Presser, P.C.

(57) ABSTRACT

An image pickup apparatus includes: an image pickup device configured to pick up an optical image formed by an objective optical system and generate an image; a cut-out range setting portion configured to set a cut-out area so that a center comes close to a field-of-view center as a zoom magnification set by an electronic zoom setting portion increases; and a zoom processing portion configured to cut out the set cut-out area from the image, perform enlargement or reduction corresponding to the zoom magnification and generate a zoomed image.

8 Claims, 9 Drawing Sheets

(51) Int. Cl.
*A61B 1/00* (2006.01)
*A61B 1/04* (2006.01)
*G02B 23/24* (2006.01)
*G03B 5/00* (2006.01)
*H04N 5/225* (2006.01)

(52) U.S. Cl.
CPC ............... *G03B 5/00* (2013.01); *H04N 5/225* (2013.01); *H04N 5/2256* (2013.01); *H04N 5/232* (2013.01); *H04N 5/23238* (2013.01); *H04N 5/23293* (2013.01); *H04N 2005/2255* (2013.01)

(56) References Cited

U.S. PATENT DOCUMENTS

| | | | |
|---|---|---|---|
| 2014/0307072 A1* | 10/2014 | Takahashi | H04N 5/23296 348/65 |
| 2015/0265136 A1 | 9/2015 | Honda | |

FOREIGN PATENT DOCUMENTS

| | | |
|---|---|---|
| JP | 4884567 B2 | 2/2012 |
| JP | 5698879 B2 | 4/2015 |
| JP | 2015-205126 A | 11/2015 |
| JP | 2015-205127 A | 11/2015 |
| WO | WO 2011/055614 | 5/2011 |
| WO | WO 2014/088076 A1 | 6/2014 |

* cited by examiner

IMAGE PICKUP APPARATUS, IMAGE PROCESSING APPARATUS, AND METHOD FOR ACTIVATING IMAGE PICKUP APPARATUS

CROSS REFERENCE TO RELATED APPLICATION

This application is a continuation application of PCT/JP2015/082132 filed on Nov. 16, 2015 and claims benefit of Japanese Application No. 2014-236899 filed in Japan on Nov. 21, 2014, the entire contents of which are incorporated herein by this reference.

BACKGROUND OF THE INVENTION

1. Field of the Invention

The present invention relates to an image pickup apparatus which cuts out, and enlarges or reduces a part of an image represented by an image pickup signal obtained by performing image pickup, an image processing apparatus and a method for activating the image pickup apparatus.

2. Description of the Related Art

Electronic zoom processing for cutting out, and enlarging or reducing a part of an image represented by an image pickup signal has been conventionally proposed, and it is widely performed to acquire an electronically enlarged image by cutting out a part of a central part of an image and performing interpolation and the like.

By the way, super-wide-angle endoscopes aiming at increasing an angle of view have been proposed recently. An endoscope which acquires a front-field-of-view image from a front-view observation window arranged on a distal end face of a cylindrical portion and acquires a side-field-of-view image from a side-view observation window arranged on a circumferential face of the cylindrical portion, for example, as described in International Publication No. WO2011/055614 is given as an example. Since the super-wide-angle endoscope described in International Publication No. WO2011/055614 has a structure in which a nozzle portion configured to clean the front-view observation window and the side-view observation window, and the like are arranged along a part of the circumferential face of the cylindrical portion, it is inevitable that optical vignetting occurs in a part of a formed optical image (for example, a part of a side field of view here).

SUMMARY OF THE INVENTION

An image pickup apparatus according to a certain aspect of the present invention includes: an image pickup portion configured to pick up an optical image of an object formed by an objective optical system configured to form the optical image of the object, and generate an image pickup signal; a zoom magnification setting portion configured to set a zoom magnification; a cut-out range setting portion configured to set a position and size of a cut-out area, which is a part of an image represented by the image pickup signal, wherein a center of the cut-out area is set at a position deviated from a field-of-view center of the objective optical system when the zoom magnification is a first magnification, and the center of the cut-out area is set to come close to the field-of-view center as the zoom magnification increases from the first magnification; and a zoom processing portion configured to cut out the cut-out area set by the cut-out range setting portion from the image represented by the image pickup signal, perform enlargement or reduction corresponding to the zoom magnification and generate a zoomed image.

An image processing apparatus according to a certain aspect of the present invention is an image processing apparatus picking up an optical image of an object formed by an objective optical system and processing a generated image pickup signal, the image processing apparatus including: a cut-out range setting portion configured to set a position and size of a cut-out area, which is a part of an image represented by the image pickup signal, wherein a center of the cut-out area is set at a position deviated from a field-of-view center of the objective optical system when a zoom magnification is a first magnification, and the center of the cut-out area is set to come close to the field-of-view center as the zoom magnification increases from the first magnification; and a zoom processing portion configured to cut out the cut-out area set by the cut-out range setting portion from the image represented by the image pickup signal, perform enlargement or reduction corresponding to the zoom magnification and generate a zoomed image.

A method for activating an image pickup apparatus according to a certain aspect of the present invention is a method including: an image pickup portion picking up an optical image of an object formed by an objective optical system configured to form the optical image of the object, and generating an image pickup signal; a zoom magnification setting portion setting a zoom magnification; a cut-out range setting portion setting a position and size of a cut-out area, which is a part of an image represented by the image pickup signal, wherein a center of the cut-out area is set at a position deviated from a field-of-view center of the objective optical system when the zoom magnification is a first magnification, and the center of the cut-out area is set to come close to the field-of-view center as the zoom magnification increases from the first magnification; and a zoom processing portion cutting out the cut-out area set by the cut-out range setting portion from the image represented by the image pickup signal, performing enlargement or reduction corresponding to the zoom magnification and generating a zoomed image.

DETAILED DESCRIPTION OF THE PREFERRED EMBODIMENT(S)

Embodiments of the present invention will be described below with reference to drawings.

First Embodiment

Figure 1:
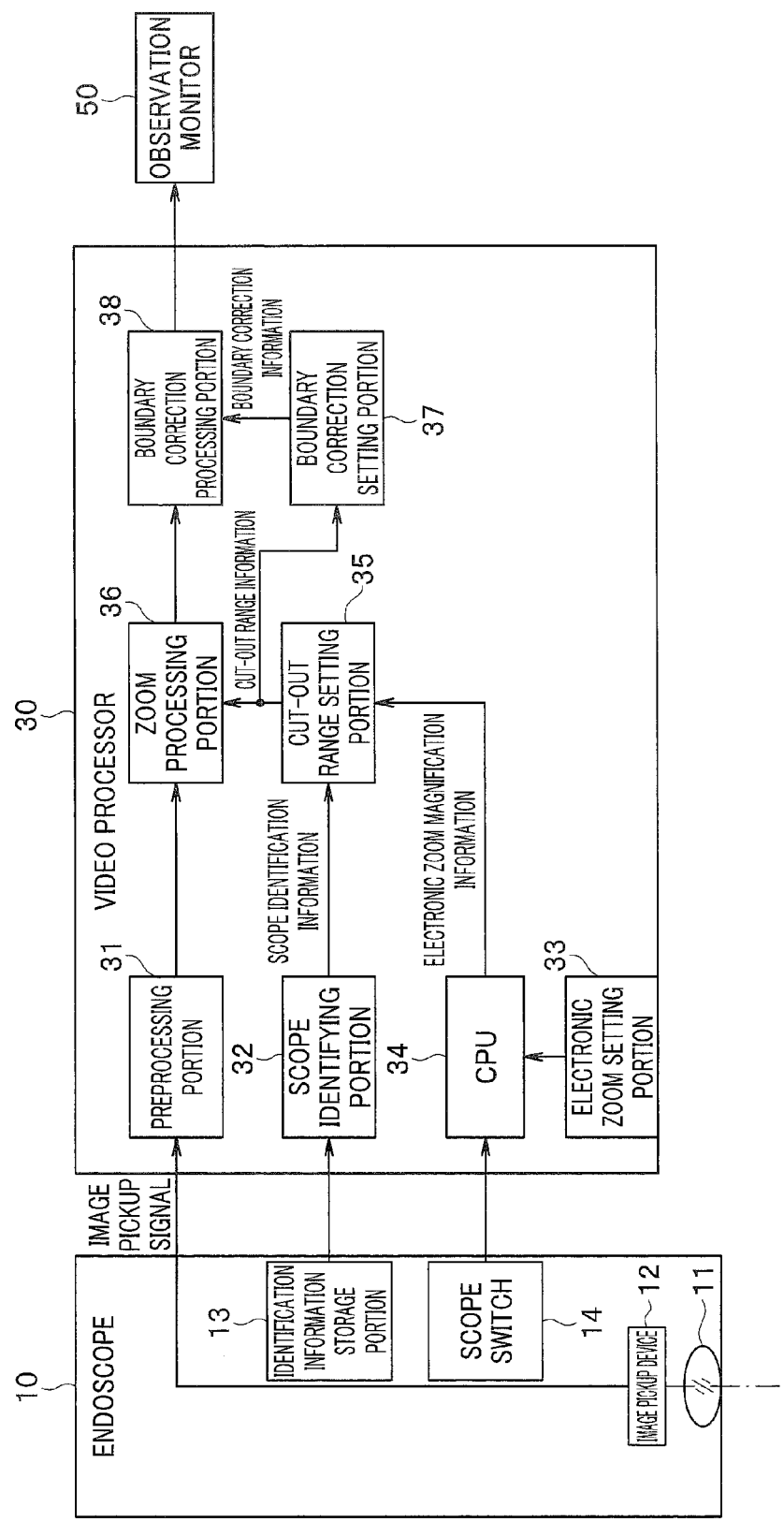
FIG. 1 is a block diagram showing a configuration of an image pickup apparatus in a first embodiment of the present invention.

FIGS. 1 to 9 show a first embodiment of the present invention, and FIG. 1 is a block diagram showing a configuration of an image pickup apparatus.

The image pickup apparatus is provided with an endoscope 10 configured to pick up an image of an object and output an image pickup signal, a video processor 30 configured to process the image pickup signal outputted from the endoscope 10 and generate a display signal, and an observation monitor 50 configured to display an observation image corresponding to the display signal generated by the video processor 30.

The endoscope 10 is provided with an objective optical system 11, an image pickup device 12, an identification information storage portion 13, and a scope switch 14.

The objective optical system 11 forms an optical image of an object.

Figure 4:
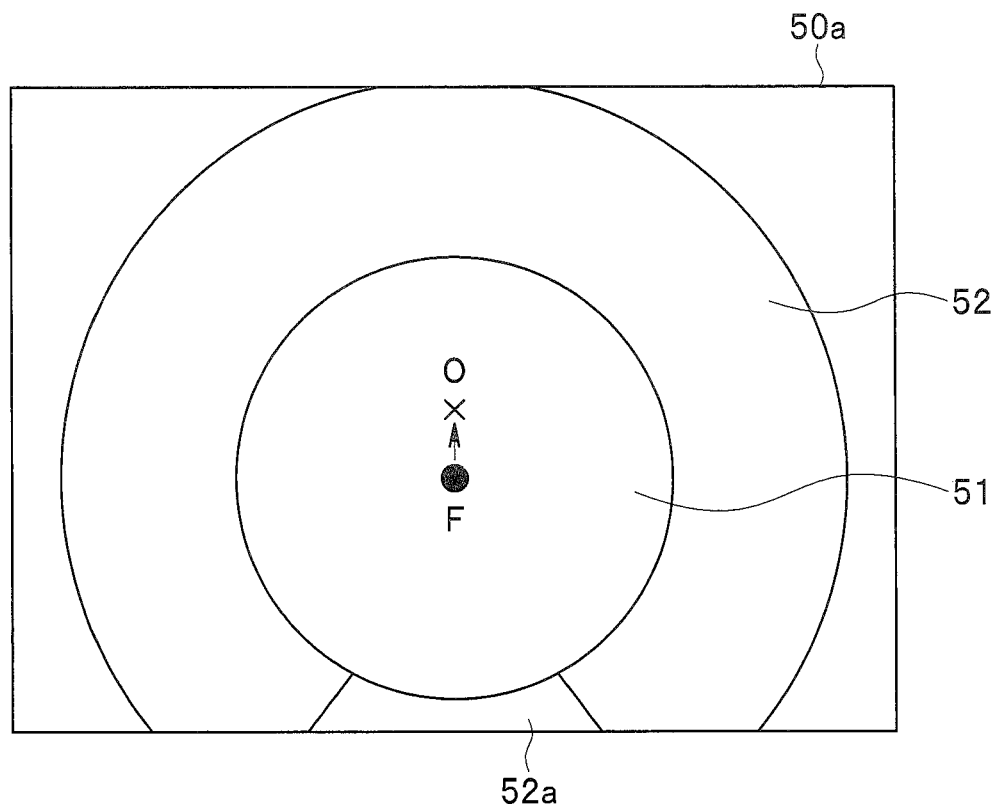
FIG. 4 is a diagram showing a state of a screen when an image represented by an image pickup signal outputted from an image pickup device is displayed on an observation monitor in the first embodiment.

The image pickup device 12 is an image pickup portion arranged so that a field-of-view center F (see FIG. 4 and the like) of the objective optical system 11 is positioned being deviated from a center of an image pickup range (which corresponds to a center O of a cut-out area in a case where a zoom magnification is 1× shown in FIG. 4) and configured to pick up an optical image of an object formed by the objective optical system 11 and generate an image pickup signal.

The identification information storage portion 13 is a storage portion configured to nonvolatilely store identification information about the endoscope 10, and a model number and a serial number of the endoscope 10, a size and the number of pixels of the image pickup device 12, arrangement information indicating a designed position of the field-of-view center F of the objective optical system 11 relative to the center of the image pickup range of the image pickup device 12, and the like are stored at time of manufacture in advance.

The scope switch 14 is a switch for performing an operation of the endoscope 10 and includes, for example, a freeze switch configured to pick up a still image, an air/water feeding switch and a zoom switch for performing an electronic zoom operation. Here, the zoom switch of the scope switch 14 functions as a zoom magnification setting portion configured to set the zoom magnification.

A configuration of the endoscope 10 will be further described with reference to FIG. 3. Here, FIG. 3 is a perspective view showing a configuration of a distal end portion 16 of an insertion portion of the endoscope 10.

The distal end portion 16 of the insertion portion is provided with a cylindrical portion 17 projecting from a distal end face in an insertion axis direction. In the cylindrical portion 17, the objective optical system 11 described above is arranged as an optical system which functions as both of a front-view optical system and a side-view optical system. That is, the objective optical system 11 is adapted to acquire a front-field-of-view image by object light of a front field of view, which is a field of view to a direction of the field-of-view center F (therefore, the field-of-view center F is a center of the front field of view), via a front-view observation window 21 arranged on the distal end face of the cylindrical portion 17 and acquire a side-field-of-view image by object light from a side field of view, which is a field of view in a lateral direction relative to the direction to the field-of-view center F, via a side-view observation window 22 arranged on a circumferential face of the cylindrical portion 17. Thus, the endoscope 10 of the present embodiment is configured as a super-wide-angle endoscope which acquires a front-field-of-view image and a side-field-of-view image.

Further, a proximal end portion of the cylindrical portion 17 is provided with a side-view illuminating window 23 configured to emit illuminating light to a side-field-of-view range from the side-view observation window 22, and a distal end face of the distal end portion 16 is provided with a front-view illuminating window 19 configured to emit illuminating light to a front-field-of-view range from the front-view observation window 21.

Figure 3:
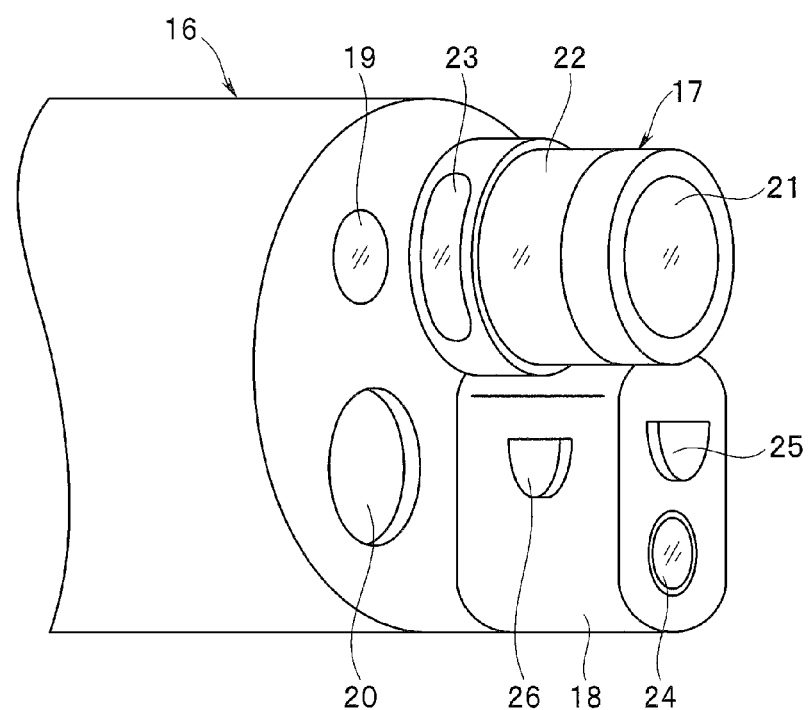
FIG. 3 is a perspective view showing a configuration of a distal end portion of an insertion portion of an endoscope in the first embodiment.

Furthermore, the distal end face of the distal end portion 16 is provided with a channel opening portion 20 of a treatment instrument channel, and a support portion 18 projecting in the insertion axis direction along a part of the circumferential face of the cylindrical portion 17 described above (adjoining the circumferential face on a lower part side of the cylindrical portion 17 in FIG. 3).

On a distal end face of the support portion 18, for example, a front-view illuminating window 24 configured to emit illuminating light to the front-field-of-view range from the front-view observation window 21 and a front-view observation window nozzle portion 25 for ejecting fluid for cleaning the front-view observation window 21 are provided. Further, on a side face of the support portion 18, a side-view observation window nozzle portion 26 for ejecting fluid for cleaning the side-view observation window 22 is provided.

The endoscope 10 configured as described above is provided with the support portion 18, which is a structure provided at such a position that a part of object light from an object is blocked from being incident on the objective optical system 11, that is, here, the support portion 18 covers a part of the circumferential face of the cylindrical portion 17 and blocks a part of object light incident from the side field of view by the side-view observation window 22, and, therefore, it is inevitable that optical vignetting occurs on a part of a formed optical image (here, for example, a part of the side field of view).

Here, FIG. 4 is a diagram showing a state of a screen 50a when an image represented by an image pickup signal outputted from the image pickup device 12 is displayed on the observation monitor 50.

As shown in FIG. 4, a front-field-of-view image 51 formed by object light from the front-view observation window 21 forms a circle with the field-of-view center F as a center. Further, a side-field-of-view image 52 formed by object light from the side-view observation window 22 is formed in an almost annular shape on an outer circumferential portion of the front-field-of-view image 51. A reason why the side-field-of-view image 52 is described here to be in an almost annular shape is that a part of the side-field-of-view image 52 in a circumferential direction shows vignetting 52a caused by the support portion 18 described above.

Therefore, the image pickup device 12 is arranged such that the center of the image pickup range is deviated from the field-of-view center F of the objective optical system 11 in an opposite direction of the vignetting 52a in order to reduce the vignetting 52a caused by the support portion 18, which is a structure, on an optical image of an object formed on the image pickup range.

Returning to description of FIG. 1, the video processor 30 is provided with a preprocessing portion 31, a scope identifying portion 32, an electronic zoom setting portion 33, a CPU 34, a cut-out range setting portion 35, a zoom processing portion 36, a boundary correction setting portion 37 and a boundary correction processing portion 38.

The preprocessing portion 31 performs various kinds of processing such as gain adjustment and A/D conversion on the pickup signal outputted from the image pickup device 12.

The scope identifying portion 32 identifies whether or not the endoscope 10 currently connected to the video processor 30 is an endoscope in which the center of the image pickup range corresponds to the field-of-view center F of the objective optical system 11, based on, for example, model number information among the pieces of identification information outputted from the identification information storage portion 13. Here, the endoscope in which the center of the image pickup range corresponds to the field-of-view center F of the objective optical system 11 is, for example, an ordinary endoscope with a single field of view, and an endoscope in which the center of the image pickup range does not correspond to the field-of-view center F of the objective optical system 11 is, for example, the super-wide-angle endoscope having the front field of view and the side field of view as shown in FIG. 3.

The electronic zoom setting portion 33 is a zoom switch for performing an electronic zoom operation and functions as the zoom magnification setting portion configured to set the zoom magnification, similarly to the zoom switch of the scope switch 14 described above. As specific configuration examples of the electronic zoom setting portion 33, an operation panel, a keyboard, a foot switch and the like are given.

The CPU 34 is a control portion configured to control the whole image pickup apparatus, including control of each portion in the video processor 30.

The cut-out range setting portion 35 sets a cut-out area, a part of a picked-up image which is an image represented by an image pickup signal, based on zoom magnification information set by the electronic zoom setting portion 33 or the scope switch 14 and acquired via the CPU 34.

Further, if the endoscope is judged to be, for example, a super-wide-angle endoscope by the scope identifying portion 32, the cut-out range setting portion 35 corrects a cut-out area to be set, using arrangement information indicating a designed position of the field-of-view center F of the objective optical system 11 relative to the center of the image pickup range of the image pickup device 12 acquired from the scope identifying portion 32.

The cut-out range setting portion 35 is adapted to set a position and size of the cut-out area so that a center O of the cut-out area comes close to the field-of-view center F as the zoom magnification increases from 1×, as described later. (Note that the cut-out range setting portion 35 may further specify the position and size of the cut-out area based on position information about the support portion 18.)

Furthermore, the cut-out range setting portion 35 outputs information about the set position and size of the cut-out area to the zoom processing portion 36 and the boundary correction setting portion 37 as cut-out range information.

The zoom processing portion 36 cuts out the cut-out area set by the cut-out range setting portion 35 from the picked-up image processed by the preprocessing portion 31 and performs enlargement or reduction according to the zoom magnification and generates a zoomed image.

Figure 2:
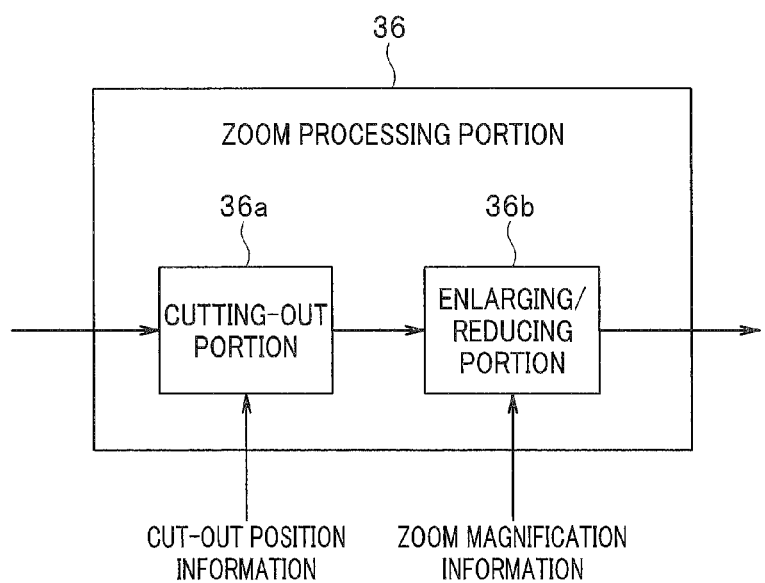
FIG. 2 is a block diagram showing an example of a configuration of a zoom processing portion in the first embodiment.

Here, FIG. 2 is a block diagram showing an example of a configuration of the zoom processing portion 36.

As shown in FIG. 2, the zoom processing portion 36 is provided with a cutting-out portion 36a and an enlarging/reducing portion 36b.

The cutting-out portion 36a cuts out the cut-out area from the image inputted from the preprocessing portion 31 based on cut-out position information (if the cut-out area is a rectangular area, the cut-out position information is, for example, configured including position information about an upper left corner of the cut-out area and position information about a lower right corner, or configured including the position information about the upper left corner of the cut-out area, the number of pixels in a horizontal direction and the number of pixels in a vertical direction, or the like) included in the cut-out range information.

The enlarging/reducing portion 36b performs pixel interpolation and the like based on the zoom magnification information acquired via the cut-out range setting portion 35 so that a pixel configuration (the number of pixels in a longitudinal direction and the number of pixels in a lateral direction) of image data of the cut-out area cut out by the cutting-out portion 36a corresponds to a pixel configuration of image data to be displayed on the observation monitor 50.

Figure 6:
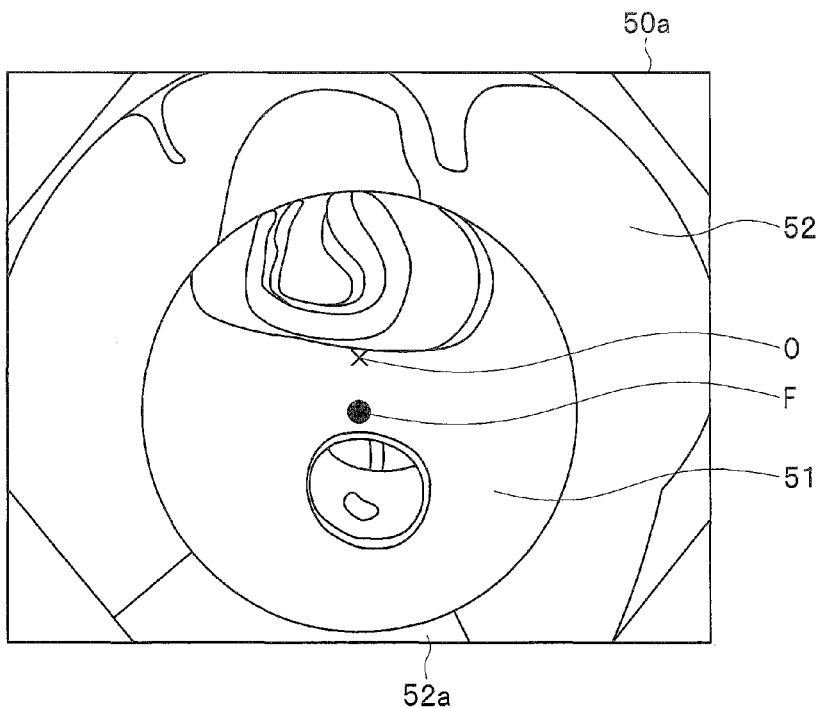
FIG. 6 is a diagram showing a display example of a screen of the observation monitor when the zoom magnification is 1× in the first embodiment.
Figure 9:
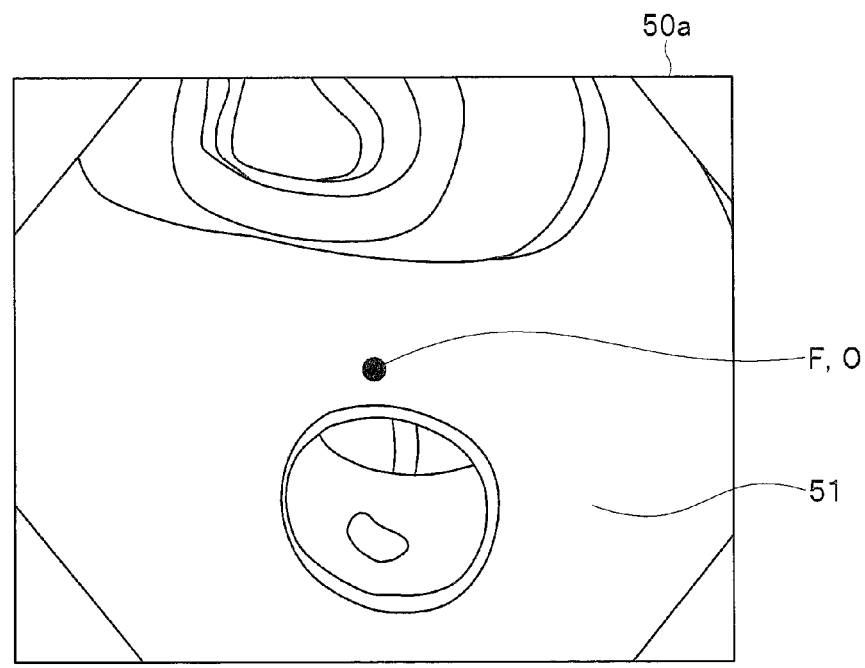
FIG. 9 is a diagram showing a display example of the screen of the observation monitor when the zoom magnification is 1.6× in the first embodiment.

The boundary correction setting portion 37 sets correction of a boundary area between the front-field-of-view image 51 and the side-field-of-view image 52. That is, when electronic zoom as shown in FIGS. 6 and 9 later is performed, a position of the boundary area between the front-field-of-view image 51 and the side-field-of-view image 52 in the cut-out area changes according to the zoom magnification. Therefore, the boundary correction setting portion 37 sets a boundary area to be a corrected boundary area as well as intensity of correction based on the cut-out range information acquired from the cut-out range setting portion 35 and outputs them to the boundary correction processing portion 38 as boundary correction information.

In order that the boundary area between the front-field-of-view image 51 and the side-field-of-view image 52 is inconspicuous, the boundary correction processing portion 38 corrects the boundary area of the image which has been zoom-processed by the zoom processing portion 36, based on the boundary correction information inputted from the boundary correction setting portion 37.

The image processed by the boundary correction processing portion 38 is outputted to the observation monitor 50 as a display signal and displayed as an observation image.

Figure 5:
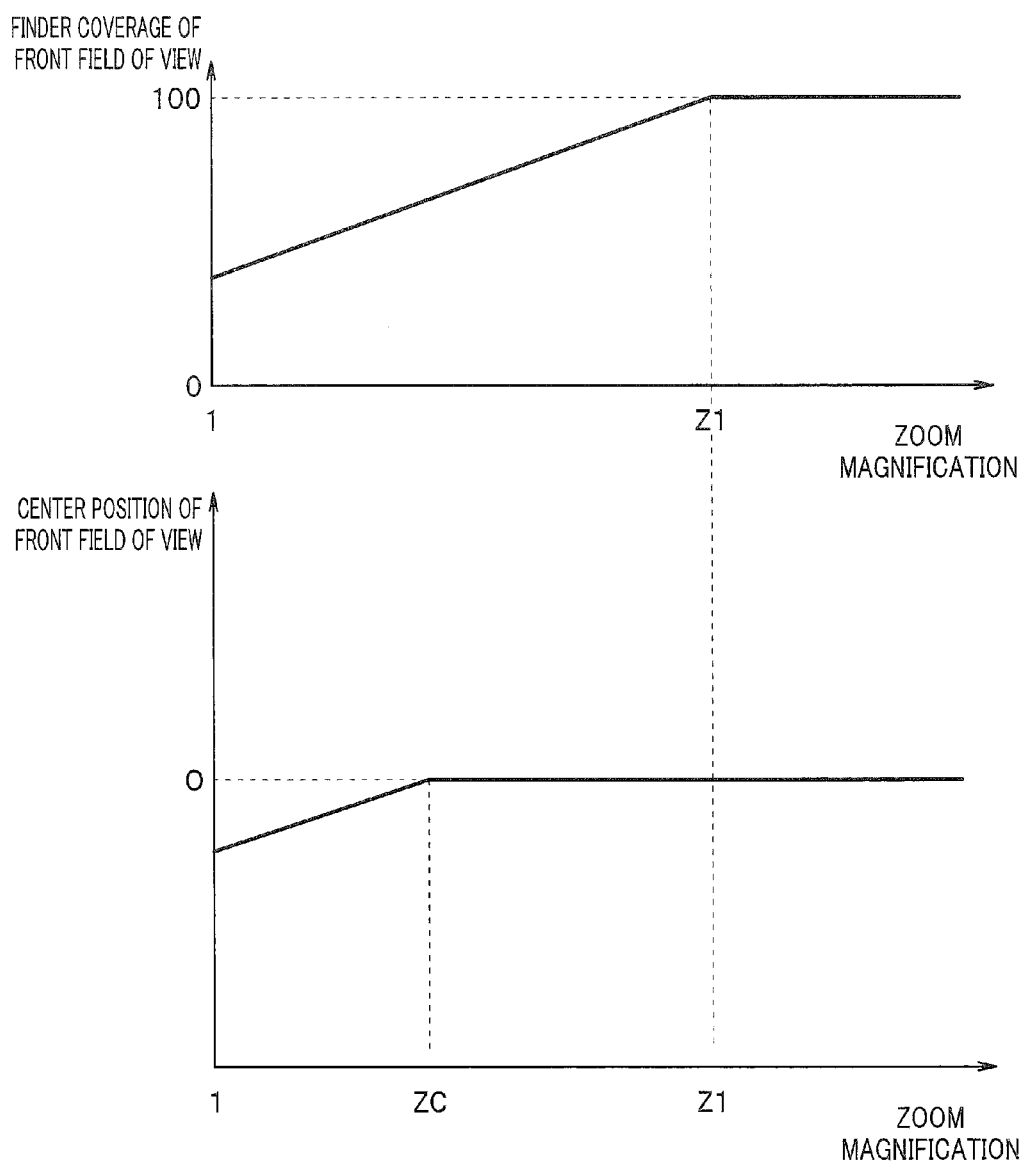
FIG. 5 is a chart showing a state that, as a zoom magnification changes, a field-of-view center comes close to a center of a cut-out area, and finder coverage of a front field of view comes close to 100%, in the first embodiment.
Figure 7:
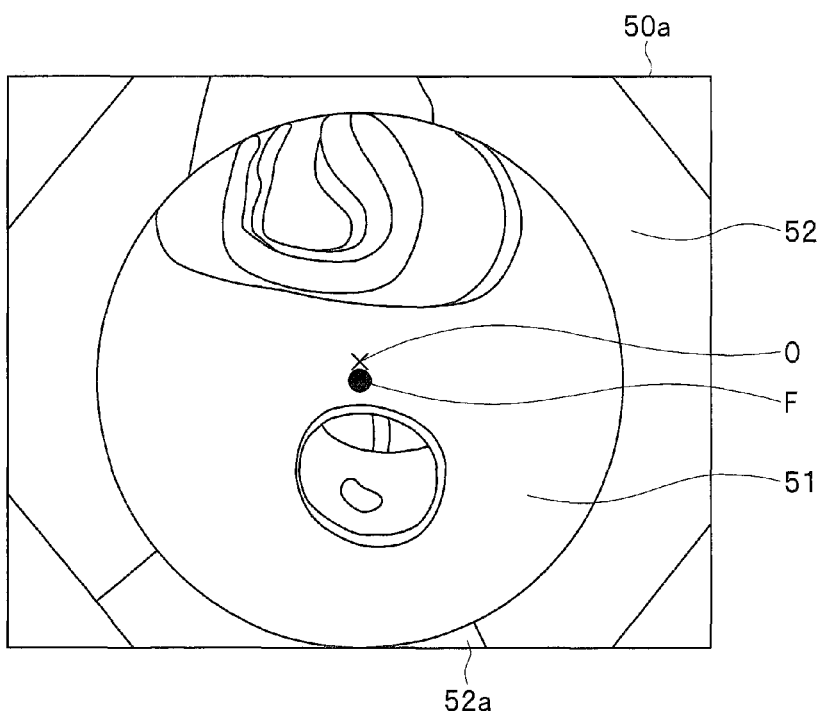
FIG. 7 is a diagram showing a display example of the screen of the observation monitor when the zoom magnification is 1.2× in the first embodiment.
Figure 8:
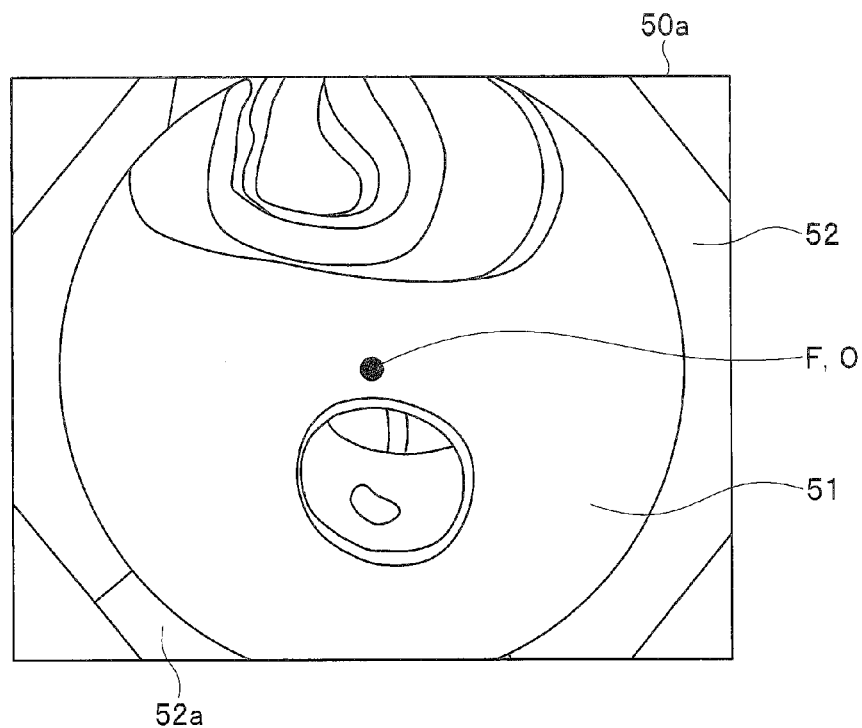
FIG. 8 is a diagram showing a display example of the screen of the observation monitor when the zoom magnification is 1.4× in the first embodiment.

Next, FIG. 5 is a chart showing a state that, as the zoom magnification changes, the field-of-view center F comes close to the center O of the cut-out area, and finder coverage of the front field of view comes close to 100%. Further, FIG. 6 is a diagram showing a display example of the screen 50a of the observation monitor 50 when the zoom magnification is 1×; FIG. 7 is a diagram showing a display example of the screen 50a on the observation monitor 50 when the zoom magnification is 1.2×; FIG. 8 is a diagram showing a display example of the screen 50a on the observation monitor 50 when the zoom magnification is 1.4×; and FIG. 9 is a diagram showing a display example of the screen 50a on the observation monitor 50 when the zoom magnification is 1.6×.

When zoom-in is not performed, and the zoom magnification is 1×, the field-of-view center F, which is a center position of the front field of view, is, for example, at a position deviated downward from the center O (which corresponds to the center of the image pickup range when the zoom magnification is 1×) of the cut-out area, and the finder coverage, which is a percentage of a front-field-of-view image occupying an endoscopic image display area on the screen 50a, is, for example, only 50% or less as shown in FIGS. 4 and 6.

When the zoom magnification increases from 1×, zoom-in is performed so that the field-of-view center F comes close to the center O of the cut-out area when seen from an observer of the observation monitor 50 as indicated by an arrow in FIG. 4 (as processing on the video processor 30 side, the cut-out area is set so that the center O of the cut-out area comes close to the field-of-view center F), and the finder coverage of the front field of view also increases as the zoom magnification increases (see FIG. 7 also).

Then, when the zoom magnification becomes ZC shown in FIG. 5, the field-of-view center F corresponds to the center O of the cut-out area, and, for example, screen display as shown in FIG. 8 is performed. In a zoom area with a zoom magnification of ZC or larger after that, the field-of-view center F remains corresponding to the center O of the cut-out area.

Furthermore, when the zoom magnification becomes Z1 shown in FIG. 5, the finder coverage of the front field of view reaches 100%. In a zoom area with a zoom magnification of Z1 or larger after that, the finder coverage of the front field of view remains 100%. Therefore, in the endoscopic image display area on the screen 50a, only the front-field-of-view image is displayed, for example, as shown in FIG. 9.

Note that Z1>ZC is satisfied in the example shown in FIG. 5, and this is because of a following reason. Since the front-field-of-view image 51 formed by object light forms, for example, a circle while the endoscopic image display area on the screen 50a forms, for example, an octagon, the vignetting 52a moves outside the field of view of the endoscopic image display area in some cases before the finder coverage of the front field of view reaches 100%. If the vignetting 52a is outside the field of view, it is not necessary that the field-of-view center F is deviated from the center O of the cut-out area even if the finder coverage is below 100%, and it is rather better to cause the field-of-view center F to correspond to the center O. However, in a case where the endoscopic image display area forms, for example, a circle, Z1=ZC is possible. On the other hand, if the finder coverage of the front field of view has reached 100%, it means that the vignetting 52a does not exist within the field of view of the endoscopic image display area. Therefore, it is not necessity that the field-of-view center F is deviated from the center O of the cut-out area, and it is not necessary that Z1<ZC is satisfied.

According to the first embodiment as described above, since a zoomed image is generated by setting a cut-out area so that the center O of the cut-out area comes close to the field-of-view center F as the zoom magnification increases, it is possible to obtain an electronically zoomed image easy to see, from an image pickup signal in which the field-of-view center F is deviated from the center of the image pickup range.

That is, it is possible to cause the vignetting 52a not to be displayed as far as possible when the zoom magnification is low, and, when the zoom magnification is high, the vignetting 52a is not displayed at all, and the field-of-view center F comes close to the center O of the cut-out area (that is, the center of the displayed screen 50a) and corresponds to the center O. Therefore, it is possible to perform electronic zoom keeping balance of display.

Then, when the finder coverage of the front field of view reaches 100%, observation can be performed with a field of view similar to that of an ordinary endoscope with a single field of view.

Second Embodiment

Figure 10:
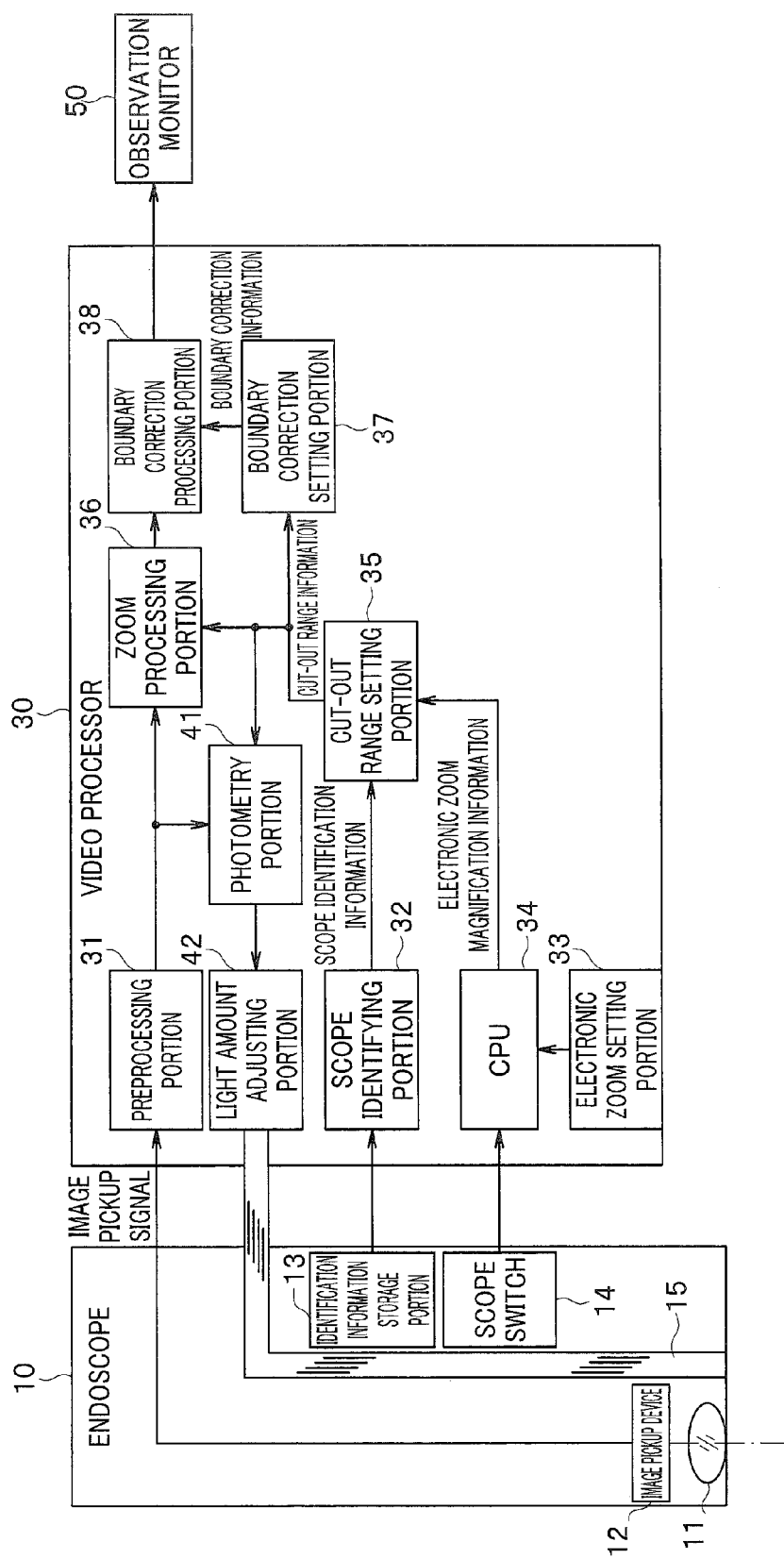
FIG. 10 is a block diagram showing a configuration of an image pickup apparatus in a second embodiment of the present invention.

FIG. 10 shows a second embodiment of the present invention and is a block diagram showing a configuration of an image pickup apparatus. In the second embodiment, portions similar to those of the first embodiment described above will be given same reference numerals, and description of the components will be appropriately omitted. Description will be made mainly on different points.

In addition to the configuration of the first embodiment described above, the present embodiment is further configured to control an amount of illuminating light emitted to an object, based on a cut-out area set by the cut-out range setting portion 35 (therefore, an image area cut out by the zoom processing portion 36 and displayed on the observation monitor 50).

First, a light guide 15 configured to transmit illuminating light is arranged in the endoscope 10 though description of the light guide 15 is omitted in the first embodiment described above, and the illuminating light is emitted from a distal end face of the light guide 15 toward an object.

Further, the video processor 30 of the present embodiment also serves as a light source apparatus configured to supply illuminating light for illuminating an object and is further provided with a photometry portion 41 and a light amount adjusting portion 42 in addition to the components of the first embodiment described above. To the light amount adjusting portion 42 between them, an incident end side of the light guide 15 described above is connected.

The photometry portion 41 acquires cut-out range information from the cut-out range setting portion 35, and performs photometry within a cut-out area specified by the cut-out range information, in an image pickup signal inputted from the preprocessing portion 31.

The light amount adjusting portion 42 emits such an amount of illuminating light that causes brightness in the cut-out area to be appropriate, to the incident end side of the light guide 15 based on a result of the photometry by the photometry portion 41.

According to the second embodiment as described above, effects almost similar to the effects of the first embodiment described above are obtained, and, since the photometry portion 41 performs photometry based on an image pickup signal of a cut-out area, it is possible to perform light adjustment appropriate for an image being observed when electronic zoom is performed.

In a case of observing, for example, an inside of an object forming a tubular shape, using the endoscope 10, a situation occurs in which a distance from the objective optical system 11 to an object surface in a front-view direction is far, but a distance to the object surface in a side-view direction is near. If the endoscope 10 is positioned too far to one side in the object forming a tubular shape, illuminating light is strongly emitted to an object part especially close in the side-view direction, and, it may happen that, for example, a blown out highlight part or a halation part occurs, and a photometry result is influenced. It is not preferable that, though such a blown out highlight part is outside the screen 50a when zoom-in is performed, a photometry result is influenced by the blown out highlight part, and an observation image is unnecessarily darkened. In comparison, according to the present embodiment, it is possible to perform appropriate light adjustment control, inhibiting influence from brightness of an object existing outside an area displayed on the screen 50a, and display an image appropriate for observation.

Third Embodiment

Figure 11:
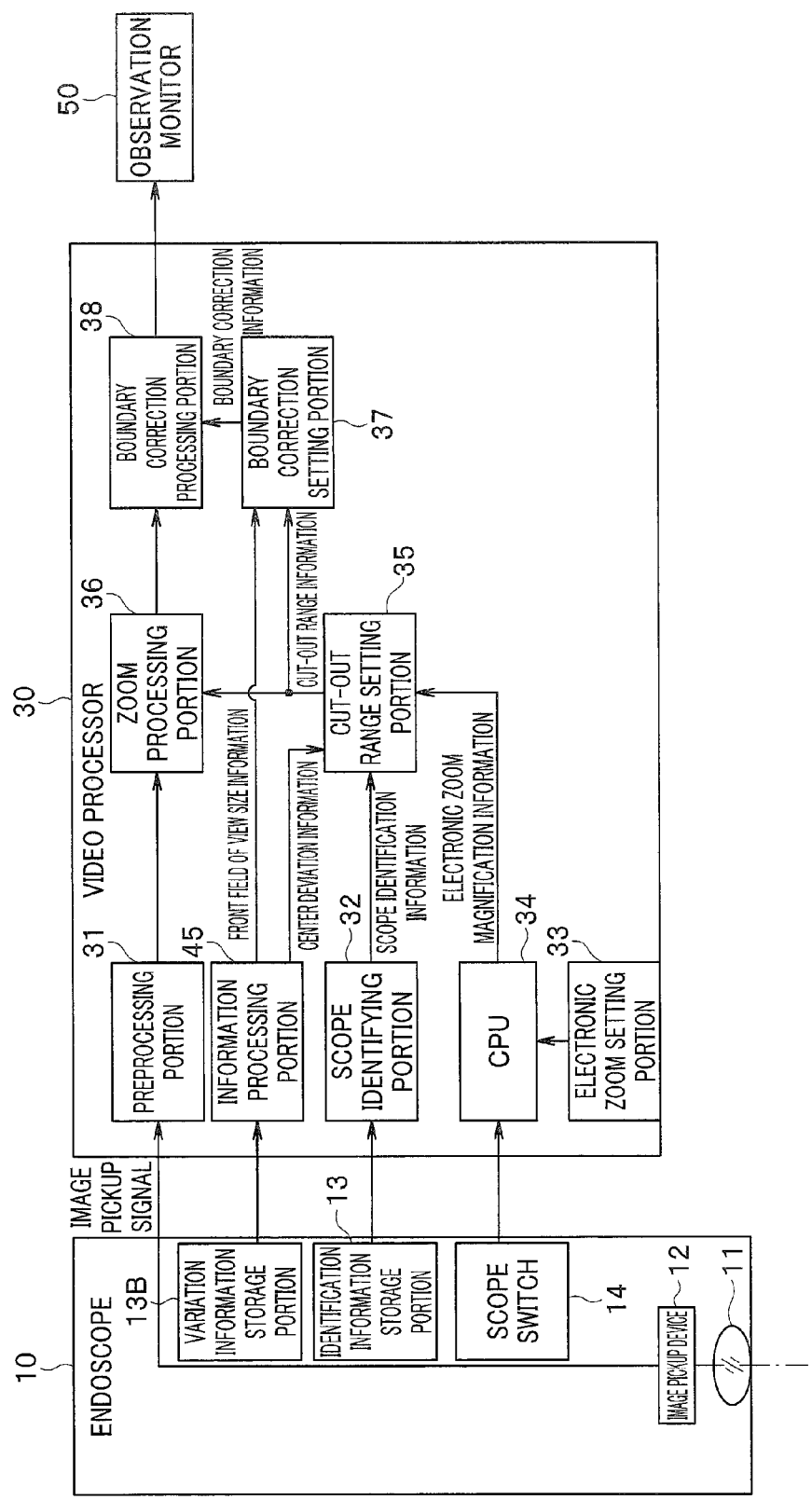
FIG. 11 is a block diagram showing a configuration of an image pickup apparatus in a third embodiment of the present invention.
Figure 12:
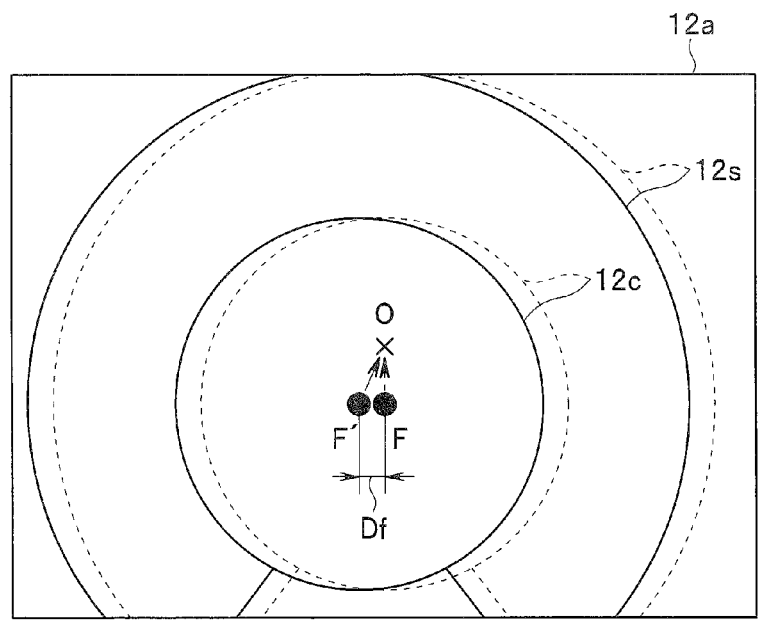
FIG. 12 is a diagram showing an example of positional deviation of a front-view optical image and a side-view optical image formed in an image pickup range of the image pickup device in the third embodiment.
Figure 13:
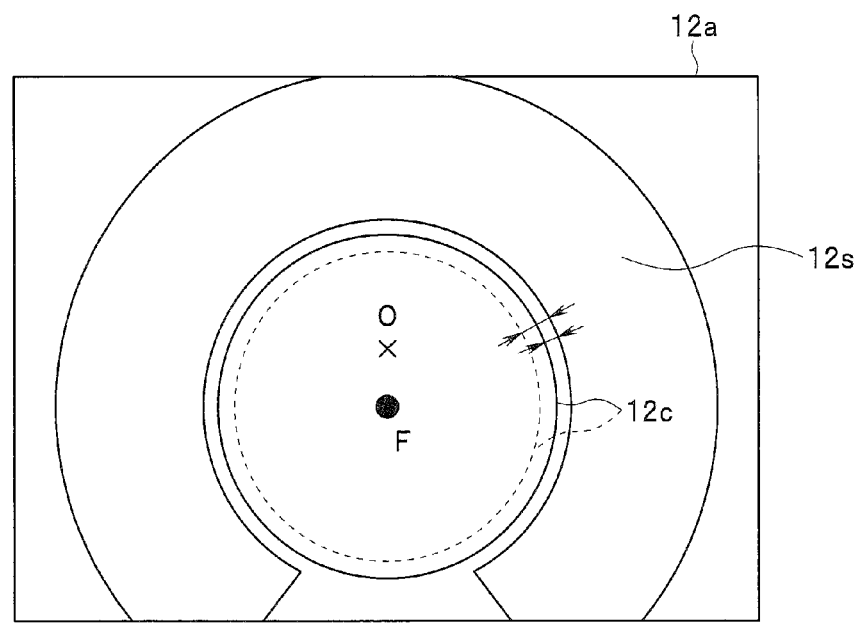
FIG. 13 is a diagram showing an example of size deviation of the front-view optical image formed in the image pickup range of the image pickup device in the third embodiment.

FIGS. 11 to 13 show a third embodiment of the present invention, and FIG. 11 is a block diagram showing a configuration of an image pickup apparatus. In the third embodiment, portions similar to those of the first and second embodiments described above will be given same reference numerals, and description of the components will be appropriately omitted. Description will be made mainly on different points.

As for a position of an optical image formed on the image pickup device 12, variation in a designed value may occur in an actual product depending on manufacturing accuracy, assembly accuracy and the like of parts constituting the endoscope 10. Therefore, in addition to the configuration of the first embodiment described above, the present embodiment is further provided with a configuration to cope with a case where deviation from a designed value occurs (for example, for each individual) for at least one of a position of the front field of view and a position of the side field of view.

That is, the endoscope 10 is further provided with a variation information storage portion 13B configured to store deviation information for each individual relative to arrangement information indicating a designed position of the field-of-view center F of the objective optical system 11 relative to a center (see the center O of the cut-out area when the zoom magnification is 1×, as shown in FIGS. 12 and 13) of an image pickup range 12a of the image pickup device 12.

The video processor 30 is further provided with an information processing portion 45 configured to read out variation information from the variation information storage portion 13B, output center deviation information to the cut-out range setting portion 35, and output front field of view size information to the boundary correction setting portion 37.

Here, FIG. 12 is a diagram showing an example of positional deviation of a front-view optical image 12c and a side-view optical image 12s formed in the image pickup range 12a of the image pickup device 12.

In FIG. 12 and FIG. 13 to be described later, reference numerals 12c and 12s indicate a front-view optical image formed on the image pickup device 12 by object light from the front-view observation window 21 and a side-view optical image formed on the image pickup device 12 by object light from the side-view observation window 22, respectively.

In the example shown in FIG. 12, the actual front-view optical image 12c and side-view optical image 12s indicated by solid lines are deviated from positions of the designed front-view optical image 12c and side-view optical image 12s indicated by dotted lines, for example, in a left direction, and a position of the field-of-view center F is deviated to a position indicated by F' in the left direction by a distance Df. (Note that, though an example where deviation occurs in the horizontal direction is shown here, it goes without saying that deviation may occur in the vertical direction in some cases.)

Further, FIG. 13 is a diagram showing an example of size deviation of the front-view optical image 12c formed in the image pickup range 12a of the image pickup device 12.

In the example shown in FIG. 13, the actual front-view optical image 12c indicated by a solid line is, for example, increased in size relative to a designed position of an optical image indicated by a dotted line, and a width of a boundary area between the front-view optical image 12c and the side-view optical image 12s (a width between an outer circumferential side outline of the front-view optical image 12c and an inner circumferential side outline of the side-view optical image 12s) is changed from a designed value.

Thus, the variation information stored in the variation information storage portion 13B includes positional deviation information about the field-of-view center F as shown in FIG. 12 and size deviation information about the front field of view as shown in FIG. 13. Referring to the variation information, the information processing portion 45 outputs the positional deviation information about the field-of-view center F to the cut-out range setting portion 35 as center deviation information and outputs the size deviation information about the front field of view to the boundary correction setting portion 37 as front field of view size information.

The cut-out range setting portion 35 sets a cut-out area based on the inputted center deviation information. As for a method for setting the cut-out area then, for example, two kinds of methods as shown below are included.

First, a first cut-out area setting method is a method in which the cut-out range setting portion 35 acquires variation information about a position of the field-of-view center F (center deviation information) to correct the position of the field-of-view center F to F', and sets a position and size of a cut-out area so that the center O of the cut-out area comes close to the position of the corrected field-of-view center F' as the zoom magnification increases from 1×.

That is, in the example shown in FIG. 12, the cut-out range setting portion 35 corrects the position of the field-of-view center F acquired from the identification information storage portion 13 as a designed value to the position of the field-of-view center F' based on the center deviation information acquired from the information processing portion 45 (information to the effect that the field-of-view center F is deviated from a designed value by the distance Df in the left direction). Then, the cut-out range setting portion 35 sets a position and size of the cut-out area so that the center O of the cut-out area comes close to the field-of-view center F' (so that the field-of-view center F' comes close to the center O of the cut-out area as indicated by an arrow in FIG. 12 when seen from an observer side of the observation monitor 50) as the zoom magnification increases from 1×.

Next, a second cut-out area setting method is a method in which the cut-out range setting portion 35 acquires the variation information about the position of the field-of-view center F, sets the position and size of a cut-out area when the zoom magnification set by the zoom magnification setting portion is 1× so that positional variation of the field-of-view center F is offset, and, furthermore, sets the position and size of the cut-out area so that the center O of the cut-out area comes close to the field-of-view center F as the zoom magnification increases from 1×.

More specifically, in the example shown in FIG. 12, since the actual position of the field-of-view center F' is deviated from the position of the field-of-view center F acquired as a designed value by the distance Df in the left direction, the cut-out range setting portion 35 causes the center O of the cut-out area to be deviated from the position shown in FIG. 12 by the distance Df in the left direction so that the variation is offset. Thereby, a designed positional relationship between O and F indicated by the dotted arrow and a positional relationship between O and F' after the variation is offset become equal.

Then, the cut-out range setting portion 35 sets, with the center O of the cut-out area as a center, a maximum cut-out area (the center of the cut-out area is O after variation is offset) that can be obtained within the image pickup range 12a and that is, for example, equal to an aspect ratio of the observation monitor 50 as a cut-out area when the zoom magnification set by the zoom magnification setting portion is 1×.

When the position and size of the cut-out area is set in this way, an image of the cut-out area is displayed on the observation monitor 50 as an image with a zoom magnification of 1×. Therefore, though a display range when the zoom magnification is 1× is different from the display range of the first and second embodiments described above and the first cut-out area setting method described above, it is not inconvenience in actual use because the deviation between F and F' is actually only little.

After that, when the zoom magnification increases from 1×, the position and size of the cut-out area is set so that the center O of the cut-out area after variation is offset comes close to the field-of-view center F as the magnification increases.

By using either the first cut-out area setting method or the second cut-out area setting method, it is possible to observe an image almost similar to that in a case where the field-of-view center F is not deviated from a designed value even if the field-of-view center F is deviated from the designed value in an actual product.

On the other hand, the front field of view size information obtained by referring to the variation information in the variation information storage portion 13B is inputted to the boundary correction setting portion 37 from the information processing portion 45.

The boundary correction setting portion 37 sets boundary correction information based on the front field of view size information inputted from the information processing portion 45 and cut-out range information inputted from the cut-out range setting portion 35.

As described above with reference to FIG. 13, the width of the boundary area between the front-view optical image 12c and the side-view optical image 12s may be different from a designed value, for example, because the size of the front-view optical image 12c is deviated from a designed value. In such a case, the boundary correction setting portion 37 corrects the size and position of the boundary area determined from designed values according to the zoom magnification based on the inputted front field of view size information and cut-out range information, and outputs the corrected boundary correction information to the boundary correction processing portion 38.

Thereby, even if the size and the like of the boundary area in an actual product is deviated from designed values, the boundary correction processing portion 38 can appropriately correction-processes the boundary area so that the boundary area between the front-field-of-view image 51 and the side-field-of-view image 52 is inconspicuous.

According to the third embodiment as described above, effects almost similar to those of the first and second embodiments described above can be obtained, and it is possible to perform appropriate display even if variation in parts and assembly of the endoscope 10 exists, because a cut-out area is set so that the center O of the cut-out area comes close to the position of the field-of-view center F according to variation of the position of the field-of-view center F.

At this time, in the case of acquiring variation information to correct the position of the field-of-view center F to F' and setting the cut-out area so that the center O of the cut-out area comes close to the position of the corrected field-of-view center F' as the zoom magnification increases from 1×, it is possible to perform 1× display without changing a maximum angle of view of the objective optical system 11.

On the other hand, in the case of setting the position and size of the cut-out area when the zoom magnification is 1× so that variation is offset, and then setting the cut-out area so that the center O of the cut-out area comes close to the field-of-view center F' as the zoom magnification increases from 1×, it is possible to perform zooming without unnaturalness in a state that an image is well-balanced (for example, well-balanced between left and right).

Note that, though description has been made above mainly on an image pickup apparatus, an image processing apparatus which performs processing similar to that of the image pickup apparatus, a method for activating the image pickup apparatus, a processing program for performing processing similar to that of the image pickup apparatus, a non-temporary computer-readable storage medium in which the processing program is recorded, and the like are also possible.

Further, the present invention is not limited to the embodiments described above as they are, and the components can be modified and embodied at an implementation phase within a range not departing from the spirit of the present invention. Further, various aspects of the invention can be formed by appropriately combining a plurality of components disclosed in each embodiment described above. For example, some components may be deleted from all the components described in each embodiment. Furthermore, components among the different embodiments may be appropriately combined. Thus, various modifications and applications are, of course, possible within the range not departing from the spirit of the invention.

What is claimed is:

1. An image pickup apparatus comprising:
   an image pickup device configured to pick up an optical image formed by an objective optical system, and to generate an image pickup signal based on the optical image that is picked up; and
   one or more processors comprising hardware, wherein the one or more processors are configured to:
   set a zoom magnification;

when setting a position and size of a cut-out area, which is a part of an image represented by the image pickup signal, set a center of the cut-out area at a position deviated from a field-of-view center of the objective optical system in a case where the zoom magnification is a first magnification, and set the center of the cut-out area so that a distance between the center of the cut-out area and the field-of-view center decreases as the zoom magnification increases from the first magnification; and cut out the cut-out area, perform enlargement processing or reduction processing according to the zoom magnification and generate a zoomed image.

2. The image pickup apparatus according to claim 1, wherein the image pickup device is arranged such that the field-of-view center is at a position deviated from a center of an image pickup range.

3. The image pickup apparatus according to claim 1, further comprising a structure provided at such a position that a part of object light from the object is blocked from being incident on the objective optical system, wherein the image pickup device is arranged such that the center of an image pickup range is deviated from the field-of-view center of the objective optical system so that vignetting caused by the structure in the optical image of the object formed within the image pickup range is reduced.

4. The image pickup apparatus according to claim 3, wherein the objective optical system is configured so that the object light from a front field of view, which is a field of view in a direction to the field-of-view center, and a side field of view, which is a field of view in a lateral direction relative to the direction to the field-of-view center, is incident; and the structure is provided at such a position that a part of the object light incident from the side field of view is blocked from being incident on the objective optical system.

5. The image pickup apparatus according to claim 1, wherein the one or more processors are configured to perform photometry of the object based on an image pickup signal of the cut-out area.

6. The image pickup apparatus according to claim 1, wherein the one or more processors are configured to:

acquire variation information about a position of the field-of-view center to correct the position of the field-of-view center; and set the position and size of the cut-out area so that a distance between the center of the cut-out area and the corrected position of the field-of-view center decreases as the zoom magnification increases from the first magnification.

7. The image pickup apparatus according to claim 1, wherein the one or more processors are configured to:

acquire variation information about a position of the field-of-view center;

set the position and size of the cut-out area when the zoom magnification set is the first magnification so that variation of the position of the field-of-view center is offset; and set the position and size of the cut-out area so that a distance between the center of the cut-out area and the field-of-view center decreases as the zoom magnification increases from the first magnification.

8. An image processing apparatus comprising:

one or more processors comprising hardware, wherein the one or more processors are configured to:

acquire an image pickup signal, wherein the image pickup signal is generated based on an optical image picked up by an image pickup device, wherein the optical image is formed by an objective optical system;

set a zoom magnification;

when setting a position and size of a cut-out area, which is a part of an image represented by the image pickup signal, set a center of the cut-out area at a position deviated from a field-of-view center of the objective optical system in a case where the zoom magnification is a first magnification, and set the center of the cut-out area so that a distance between the center of the cut-out area and the field-of-view center decreases as the zoom magnification increases from the first magnification; and cut out the cut-out area, perform enlargement processing or reduction processing according to the zoom magnification and generate a zoomed image.

* * * * *